United States Patent [19]

Abou-Gharbia et al.

[11] Patent Number: 4,798,896

[45] Date of Patent: Jan. 17, 1989

[54] ANTIPSYCHOTIC GAMMA-CARBOLINE N-OXIDES

[75] Inventors: Magid A. Abou-Gharbia, Wilmington, Del.; John P. Yardley, Gulph Mills; Cesario O. Tio, Coatesville, both of Pa.

[73] Assignee: American Home Products Corporation, New York, N.Y.

[21] Appl. No.: 145,426

[22] Filed: Jan. 19, 1988

[51] Int. Cl.$^4$ .............................................. C07D 471/04
[52] U.S. Cl. ........................................... 546/87; 546/86
[58] Field of Search .................................... 546/86, 87

[56] References Cited

U.S. PATENT DOCUMENTS

| 4,001,263 | 1/1977 | Plattner et al. | 546/85 |
| 4,110,455 | 8/1978 | von Bebenburg et al. | 546/297 |
| 4,224,329 | 9/1980 | Welsch, Jr. | 546/85 |
| 4,636,563 | 1/1987 | Abou-Gharbia | 546/85 |
| 4,672,117 | 6/1987 | Abou-Gharbia et al. | 546/85 |

OTHER PUBLICATIONS

March, *Advanced Organic Chemistry*, 1985, 3rd Edition, p. 1088.

Primary Examiner—Mary C. Lee
Assistant Examiner—Zinna Northington
Attorney, Agent, or Firm—Richard K. Jackson

[57] ABSTRACT

This invention provides a group of antipsychotic/anxiolytic agents of the formula.

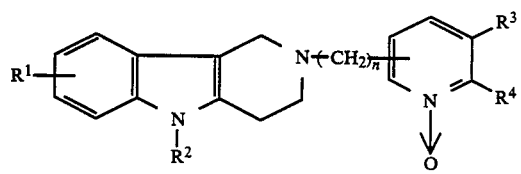

in which
$R^1$ is hydrogen, halogen, hydroxy, alkoxy or alkyl;
$R^2$ is hydrogen, phenyl or phenyl substituted with an alkyl, alkoxy, halogen, trifluoromethyl, cyano or nitro group;
$R^3$ and $R^4$ are hydrogen or, together, complete the benzo ring; and
n is 1 to 7;
or a pharmaceutically acceptable salt thereof.

3 Claims, No Drawings

ANTIPSYCHOTIC GAMMA-CARBOLINE N-OXIDES

Gamma-carbolines possessing central nervous system activity are known. Representative of such compounds are the 2-phenyl(oxy or oxo)alkyl substituted 5-aryl-tetra- and hexahydro-pyrido[4,3-b]indoles disclosed in U.S. Pat. Nos. 4,001,263 and 4,224,329. More recently, gamma-carboline antipsychotic/anxiolytic agents with very low potential for extrapyramidal side effects have appeared in U.S. Pat. Nos. 4,636,563 and 4,672,117. The biological properties of these more recently discovered compounds are discussed by Abou-Garbia, et al., in J. Med. Chem. 30 1818 (1987).

DESCRIPTION OF THE INVENTION

In accordance with this invention, there is provided a group of antipsychotic gamma-carboline N-oxides of the formula.

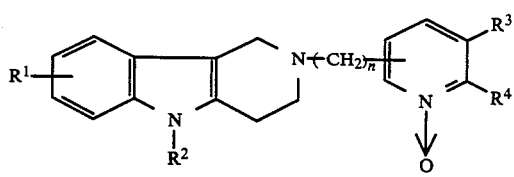

in which
$R^1$ is hydrogen, halogen, hydroxy, alkoxy of 1 to 6 carbon atoms, or alkyl of 1 to 6 carbon atoms;
$R^2$ is hydrogen, phenyl or phenyl substituted by a methyl, ethyl, methoxy, ethoxy, halogen, trifluoromethyl, cyano or nitro group;
$R^3$ and $R^4$ are hydrogen, or, when taken together, butadienylene; and
n is one of the integers 1, 2, 3, 4, 5, 6 or 7, or a pharmaceutically acceptable salt thereof.

In the proceding description of the compounds of this invention, the term "halogen" is intended to embrace chlorine, bromine and fluorine and the pharmaceutically acceptable salts are those derived from such organic and inorganic acids as: acetic, lactic, citric, tartaric, succinic, maleic, fumaric, malonic, gluconic, hydrochloric, hydrobromic, phosphoric, nitric, sulfuric, methane sulfonic, and similarly known acceptable acids.

The preferred compounds embraced by the foregoing genus genus are those in which $R^1$ is hydrogen or a halogen (the most preferred being fluorine in 8-position), $R^2$ is hydrogen, phenyl or halophenyl (the most preferred being hydrogen or 4-fluorophenyl) and n is 2, 3 or 4.

By comparative analysis, the compounds of this invention were discovered to be one major form of several metabolites of the compounds disclosed in U.S. Pat. Nos. 4,636,563 and 4,672,117. This may be illustrated by consideration of the metabolic conversion of the compound of claim 13 of U.S. Pat. No. 4,636,563. Oral administration of the drug 8-fluoro-2,3,4,5-tetrahydro-2-[3-(3-pyridinyl)propyl]-1H-pyrido[4,3-b]indole to rats at a dose of 100 milligrams per kg followed by collectiion of urine and isolation of metabolites by column chromatography and selective solubilization in organic solvents yielded several metabolites. By titanium trichloride (TiCl$_3$) reduction to the original drug administered, mass spectroscopy and NMR analysis, one of the major metabolites was deduced to contain oxygen bound to the tertiary nitrogen of pyridine. Comparison of the infrared spectrum of the pyridine N-oxide synthetically prepared, infra, demonstrated that it was in fact that same as the metabolite isolated from 8-fluoro-2,3,4,5-tetrahydro-2-[3-(3-pyridinyl)propyl]-1H-pyrido[4,3-b]indole. Subsequently, 8-fluoro-2,3,4,5-tetrahydro-2-[3-(3-pyridinyl)propyl]-1H-piperidino[4,3-b]indole N-oxide was also detected in monkey urine and plasma after intragastric administration of 4 mg/kg or iv administration of 1 mg/kg of 8-fluoro-2,3,4,5-tetrahydro-2-[3-(3-pyridinyl)propyl]-1H-piperidino[4,3-b]indole. This metabolic pathway is consistent with the other anti-psychotic-anxilytic agents disclosed and claimed in U.S. Pat. Nos. 4,636,563 and 4,672,117.

The compounds of this invention are produced from the compounds disclosed in U.S. Pat. Nos. 4,636,563 and 4,672,117 by protection of the indolic nitrogen atom, when $R^2$ is hydrogen, with a benzene sulfonyl protecting group. Then the two tertiary nitrogen atoms are oxidized with m-chloroperbenzoic acid in $CH_2Cl_2$ to obtain the di-N-oxide. Selective reduction of the basic carboline-N-oxide with $SO_2$ in $CHCl_3$ affords the pyridine-N-oxide.

The following examples illustrate, without limitation, the method employed in the preparation of several N-oxides of 8-fluoro-2,3,4,5-tetrahydro-2-[3-(3-pyridinyl)propyl]-1H-piperidine[4,3-b]indole, which N-oxides are represenatative of the other compounds embraced by the genus disclosed herein with regard to their production and relative activity profile.

EXAMPLE 1

8-Fluoro-2,3,4,5-tetrahydro-5-(phenylsulfonyl)-2-[3-(3-pyridinyl)propyl]-1H-piperidino[4,3-b]indole N,2-dioxide 8-Fluoro-2,3,4,5-tetrahydro-2-[3-(3-pyridinyl)-propyl]-1H-piperidino[4,3-b]indole monohydrochloride (10.4 g; 0.03 mol) was added to a stirred slurry of 1.9 g; 0.08 mol of 60 percent sodium hydride in 200 ml of dimethyl formamide. The mixture was stirred for five hours at room temperature, at which time benzenesulfonyl chloride (5.5 ml, 7.4 g, 0.04 mol) was added and the mixture was stirred overnight. The dimethylformamide was removed under reduced pressure and the residue was dissolved in 300 ml of methylene chloride, washed with water and dried over anhydrous sodium sulfate. The methylene chloride solution was removed in vacuo and the residue was chromatographed through 400 g of silica gel, using 5 percent methanol-ethyl acetate as the eluent. The product containing eluate fractions were collected and evaporated to afford 8-fluoro-2,3,4,5-tetrahydro-5-(phenylsulfonyl)-2-[3-(3-pyridinyl)propyl]-1H-piperidino[4,3-b]indole as a yellow solid which was recrystallized from ethyl acetate; m.p. 110°–112° C. (9 g, 70 percent yield).

Elemental analysis for $C_{25}H_{24}FN_3SO_2$: Calc'd: C, 66.74; H, 5.38; N, 9.34. Found: C, 66.90; H, 5.30; N, 9.39.

The free base was converted to the dihydrochloride, hemihydrate with ethanolic HCl; m.p. 263°–265° C.

Elemental analysis for $C_{25}H_{24}FN_3SO_2 \cdot 2HCl \cdot \frac{1}{2}H_2O$: Calc'd: C, 56.49; H, 5.12; N, 7.90; Cl, 13.34. Found: C, 56.38; H, 5.29; N, 7.77; Cl, 13.14.

The free base produced in the preceding paragraph (4.5 g; 0.01 mol) was dissolved in 150 ml of methylene chloride. m-Chloroperbenzoic acid (4.2 g; 0.022 mol) was added and the reaction mixture was stirred for three hours at room temperature. The solvent was then removed by evaporation and the residue was chromatographed through 250 g of silica gel employing 30 percent methanol-ethyl acetate as the eluent. The product containing fractions were collected and the eluent removed by evaporation under reduced pressure to afford a white solid which was recrystallized from acetone to give 3.1 g (65 percent yield) of the title compound as a monohydrate; m.p. 146°–148° C.

Elemental analysis for $C_{25}H_{24}FN_3SO_4 \cdot H_2O$: Calc'd: C, 60.11; H, 5.24; N, 8.41. Found: C, 60.35; H, 5.33; N, 8.34.

EXAMPLE 2

8-Fluoro-2,3,4,5-tetrahydro-2-[3-(3-pyridinyl)propyl]-1H-piperidino[4,3-b]indole N,2-dioxide Twelve grams of metallic sodium were dissolved in 500 ml of methanol. To this solution was added 3 g of the product of Example 1 and the mixture was refluxed overnight. The reaction mixture was cooled and 15 ml $H_2O$ was added. The solvent was removed and the residue dissolved in 50 ml $H_2O$ and extracted with ethyl acetate. The ethyl acetate was dried over anhydrous $Na_2SO_4$ and evaporated. The residue was chromatographed on silica gel using methanol as the eluent. The product containing fractions were collected and recovered from methanol to give the title compound; m.p. 114°–119° C.; MS, m/e 341 (M+).

EXAMPLE 3

8-Fluoro-2,3,4,5-tetrahydro-2-[3-(3-pyridinyl)propyl]-1H-piperidino[4,3-b]indole N-oxide The product of Example 1 (3 g; 0.01 mol) was dissolved in 150 ml of chloroform and the solution was saturated with gaseous $SO_2$ at ice bath temperature. The reaction mixture was stirred at 2° C. overnight, after which time 100 ml of 10 percent NaOH solution was added with continuous cooling and stirring for 20 minutes. The organic layer was then separated, washed with water and dried over anhydrous $Na_2SO_4$. The solvent was then removed in vacuo and the residue recrystallized from methanol to afford 1.85 g (38 percent yield) of 8-fluoro-2,3,4,5-tetrahydro-5-(phenylsulfonyl)-2-[3-(3-pyridinyl)propyl]-1H-piperidino[4,3-b]indole N-oxide; m.p. 173°–175° C.

Elemental analysis for $C_{25}H_{24}FN_3SO_3$: Calc'd: C, 64.49; H, 5.19; N, 9.02. Found: C, 64.25; H, 5.27; N, 8.94.

A solution of 12 g of sodium in 500 ml of anhydrous methanol, to which the product of the preceding paragraph (3 g, 0.01 mol) had been added, was refluxed overnight. The methanol was removed under reduced pressure and the residue was dissolved in 50 ml of water, extracted into ethyl acetate, washed with brine and dried over anhydrous $Na_2SO_4$. The ethyl acetate was removed in vacuo and the residue was recrystallized from methanol-ethyl acetate (1:1 mixture) to afford 2 g (63 percent yield) of the title compound; m.p. 202°–204° C.

Elemental analysis for $C_{19}H_{20}FN_3O$: Calc'd: C, 70.12; H, 6.19; N, 12.90. Found: C, 70.19; H, 6.23; N, 13.00.

EXAMPLE 4

8-Fluoro-2,3,4,5-tetrahydro-2-[3-(3-pyridinyl)propyl]-1H-piperidino[4,3-b]indole 2-oxide To a solution of 8-fluoro-2,3,4,5-tetrahydro-5-(phenylsulfonyl)-2-[3-(3-pyridinyl)propyl]-1H-piperidino[4,3-b]indole (4.5 g; 0.01 mol) in 150 ml of methylene chloride was added one equivalent of m-chloroperbenzoic acid (2.1 g; 0.01 mol) and the reaction mixture was stirred for three hours at room temperature. The solvent was removed and the residue was chromatographed through 250 g of silica gel using 30 percent methanol-ethyl acetate as the eluent. The product containing fractions were collected and evaporated under reduced pressure to afford 8-fluoro-2,3,4,5-tetrahydro-5-(phenylsulfonyl)-2-[3-(3-pyridinyl)propyl]-1H-piperidino[4,3-b]indole 2-oxide as a solid monohydrate which was recrystallized from acetone; m.p. 136°–138° C.

Elemental analysis for $C_{25}H_{24}FN_3SO_3 \cdot H_2O$: Calc'd: C, 62.03; H, 5.41; N, 8.68. Found: C, 61.83; H, 5.30; N, 8.10.

To the product of the preceding paragraph (2 g; 0.01 mol) in 400 ml methanol was added in three 1.5 hour intervals, dibasic sodium phosphate (3×5 g) and 8 percent sodium amalgam (3×3 g) with stirring. The reaction mixture was filtered and the solvent was removed by evaporation. The residue was chromatographed through 100 g of silica gel using methanol as the eluent. The product containing fractions were collected and evaporated under reduced pressure to afford 800 mg of the title compound, which was dissolved in methanol and precipitated with diethyl ether. The solid was removed by filtration and recrystallized from an ethanol-acetone (1:1) mixture to give the title compound; m.p. 168°–170° C.

Elemental analysis for $C_{19}H_{20}FN_3O$: Calc'd: C, 70.12; H, 6.19; N, 12.90. Found: C, 69.30; H, 6.38; N, 12.32.

The antipsychotic/anxiolytic properties of the pyridine N-oxides of this invention were established by standard pharmacologically accepted procedures involving conditioned avoidance studies in which trained male CD rats (Charles River), 400–500 gm body weight, are exposed to a fifteen second warning tone (conditional stimulus) continued for an additional fifteen seconds accompanied by electric shock. The rates can avoid the electric shock by jumping to an exposed shelft (shelf-jump response). A response during the initial warning tone is considered to be an avoidance response while a response during shock delivery is considered an escape response. The avoidance response is determined and expressed as a percentage of total trials from an appropriate number of trials. The shelf-jump response test procedure follows that of Herman et al., Comm. in Psychopharm., 3, 165 (1979).

Following the procedures of Fields et al., Brain Res., 136, 578 (1977) and Yamamura et al., Neurotransmitter Receptor Binding, Raven Press, N.Y. (1978), homogenized limbic brain tissue is incubated with $^3H$-spiroperidol and various concentrations of test compound, filtered and washed and shaken with Hydrofluor scintillation cocktail (National Diagnostics) and counted in a Packard 460 CD scintillation counter. Binding in the presence of test compound is expressed as percent of specific binding [total binding less binding in the presence of 1 μM (+) butaclamol]. This limbic $D_2$ binding procedure assesses a compounds potential binding at dopamine receptors as a predictor of antipsychotic activity. In an analogous test procedure employing brain cortical tissue, the compounds of this invention, which have been tested, demonstrated approximately the same potency as serotonin for binding at serotonin-2 receptors [dopamine is inactive at this receptor while serotonin exhibits a $K_i$ of 20 (14–30)$\mu M$].

Of the tertiary nitrogen oxides from the parent molecules, surprisingly, only the N-oxide possesses meaningful antipsychotic/anxiolytic activity when subjected to these standard pharmacological conditioned avoidance serotonin binding inhibition and dopamine receptor binding inhibition procedures.

The results of these test procedures are reported in the following Table where A is the parent compound 8-fluoro-2,3,4,5-tetrahydro-2-[3-(3-pyridinyl)propyl]-1H-piperidino(4,3-b]indole; B is the 2, N-dioxide; C is the 2-oxide and D is the N-oxide representative of the compounds claimed herein:

TABLE

| Compound | Inhibition of shelf-jump | % Inhibition of accumbens $D_2$ 1 $\mu M$ | % Inhibition of of serotonin $5HT_2$ binding at 1 $\mu M$ |
| --- | --- | --- | --- |
| A | 73% at 20 mg/kg | 93% | 78% |
| B | not run | 4% | 18% |
| C | not significant | 0% | 18% |
| D | 16% at 40 mg/kg | 66% | 68% |

From these data, the activity profile of the compounds of this invention are seen to be that of antipsychotic/anxiolytic agents useful in the treatment of psychoses such as paranoia and schizophrenia and in alleviating anxiety. As such, they may be administered neat or with a pharmaceutical carrier to a patient in need thereof. The pharmaceutical carrier may be solid or liquid.

A solid carrier can include one or more substances which may also act as flavoring agents, lubricants, solubilizers, suspending agents, fillers, glidants, compression aids, binders of tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and sized desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both of pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oil ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. When the compound is orally active, it can be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or table itself, or it can be the appropriate number of any such compositions in package form.

The dosage to be used in the treatment of a specific psychosis must be subjectively determined by the attending physician. The variables involved include the specific psychosis or state of anxiety and the size, age and response pattern of the patient.

What is claimed is:

1. A compound of the formula:

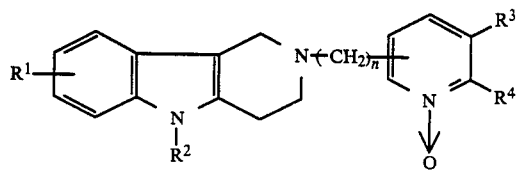

in which $R^1$ is hydrogen, halogen, hydroxy, alkoxy of 1 to 6 carbon atoms, or alkyl of 1 to 6 carbon atoms;

$R^2$ is hydrogen, phenyl or phenyl substituted by a methyl, ethyl, methoxy, ethoxy, halogen, trifluoromethyl, cyano or nitro group;

$R^3$ and $R^4$ are hydrogen, or, when taken together, butadienylene; and n is one of the integers 1, 2, 3, 4, 5, 6 or 7, or a pharmaceutically acceptable salt thereof.

2. A compound of claim 1 of the formula:

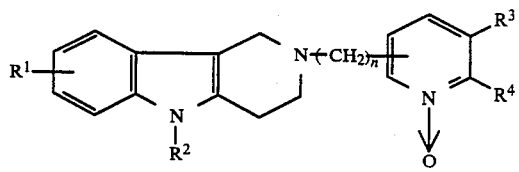

in which $R^1$ is hydrogen or a halogen;

$R^2$ is hydrogen, phenyl or halphenyl and n is 2, 3 or 4.

3. The compound of claim 1 which is 8-fluoro-2,3,4,5-tetrahydro-2-[3-(3-pyridinyl)propyl]-1H-piperidino[4,3-b]indole N-oxide.

* * * * *